US006764850B2

(12) United States Patent
Maxwell et al.

(10) Patent No.: US 6,764,850 B2
(45) Date of Patent: Jul. 20, 2004

(54) SAMPLE CONTACT PLATE WITH LATCHABLE COVER

(75) Inventors: Douglas E. Maxwell, Itasca, IL (US); Frank Cammarata, III, Cary, IL (US); Anthony J. Donovan, Bartlett, IL (US)

(73) Assignee: bioMerieux, Inc., Durham, NC (US)

( * ) Notice: Subject to any disclaimer, the term of this patent is extended or adjusted under 35 U.S.C. 154(b) by 0 days.

(21) Appl. No.: 10/622,397

(22) Filed: Jul. 18, 2003

(65) Prior Publication Data

US 2004/0018616 A1 Jan. 29, 2004

Related U.S. Application Data

(63) Continuation of application No. 10/178,422, filed on Jun. 24, 2002, now Pat. No. 6,602,704.

(51) Int. Cl.[7] .............................................. C12M 1/22
(52) U.S. Cl. ............................... 435/305.3; 435/305.4; 435/309.4
(58) Field of Search ........................ 435/288.3, 288.4, 435/305.1, 305.2, 305.3, 305.4, 309.1, 309.4

(56) References Cited

U.S. PATENT DOCUMENTS

| 238,886 | A |  | 2/1881 | Goy |
| 272,185 | A |  | 1/1883 | Schlesinger |
| 295,319 | A |  | 4/1884 | Franchere et al. |
| 316,752 | A |  | 5/1885 | Ricketts |
| 452,624 | A |  | 5/1891 | Choi |
| 2,677,646 | A |  | 5/1954 | Lovell et al. |
| 2,971,892 | A |  | 2/1961 | Carski et al. |
| 3,649,463 | A |  | 3/1972 | Buterbaugh et al. |
| 3,729,382 | A |  | 4/1973 | Shaffer et al. |
| 3,769,936 | A |  | 11/1973 | Swanson et al. |
| 4,160,700 | A |  | 7/1979 | Boomus et al. |
| 4,255,522 | A |  | 3/1981 | Fusenig et al. |
| 4,743,556 | A |  | 5/1988 | Ervin |
| 4,945,061 | A |  | 7/1990 | Iskander |
| 4,988,302 | A |  | 1/1991 | Smith et al. |
| 5,021,351 | A |  | 6/1991 | Ervin |
| 5,134,064 | A |  | 7/1992 | Nordlund |
| 5,700,655 | A |  | 12/1997 | Croteau et al. |
| 5,854,065 | A |  | 12/1998 | Livingston et al. |
| 5,928,858 | A |  | 7/1999 | Chao |
| 6,602,704 | B1 | * | 8/2003 | Maxwell et al. .......... 435/305.4 |

* cited by examiner

*Primary Examiner*—David A. Redding
(74) *Attorney, Agent, or Firm*—Samir R. Patel

(57) ABSTRACT

Contact plates are provided including a base member and a lid. The base member has a sidewall extending circumferentially around a peripheral edge portion thereof to define a sample receiving area. The lid has a sidewall extending circumferentially around a peripheral edge portion thereof. A plurality of ribs extend from an inner surface of the sidewall of the lid. The ribs are configured to provide an interference fit engagement between the sidewall of the base member and the sidewall of the lid when the lid is attached to the base member.

11 Claims, 5 Drawing Sheets

SAMPLE CONTACT PLATE WITH LATCHABLE COVER

This application is a continuation of application Ser. No. 10/178,422, filed June 24, 2002, now U.S. Pat. 6,602,704.

FIELD OF THE INVENTION

The present invention relates to devices for holding samples and, more particularly, to contact plates with lids for enclosing samples, such as microorganisms.

BACKGROUND OF THE INVENTION

A variety of sampling devices have been developed over the years for holding an agar media, or the like, in order to test whether microorganisms are present in a sample. One problem encountered with existing sampling devices is that the person who is using the device may have difficulty handling the sampling device and the sample without introducing contaminants that might affect the test.

Another difficulty associated with conventional sampling devices is that it often becomes hard to remove a lid from a dish because of a moisture seal lock. However, the opposite problem, the lid being inadvertently detached or removed when it is desired to maintain the sampling device in a covered state, may also be encountered with known sampling devices, which may adversely affect the ability to maintain, handle and/or store the sampling devices.

U.S. Pat. No. 5,854,065 describes one known type of microorganism sampling device. A base member is provided with a continuous sidewall providing a holding area for the agar media. A peripheral support surface extends around the base member at the external diameter of the base member outside the continuous sidewall. The lid member of the sampling device has a flange extending around the external diameter thereof, which includes a plurality of lugs downwardly extending therefrom that contact the peripheral support surface of the base member when the lid member is attached and define a gap allowing for airflow between the lid and base member to inhibit the creation of a moisture seal lock.

The count-tact Plate™ from bioMerieux, Inc. of France is a further type of microorganism sampling device. The count-tact Plate™ includes a base member with a continuous sidewall providing a holding area. The base member sidewall includes a plurality of ribs extending from an outer surface thereof that are contacted by the lid of the count-tact Plate™ when the lid is pressed onto the base member by a user. The ribs may, thus, operate to removably connect the lid to the base member.

SUMMARY OF THE INVENTION

According to embodiments of the present invention, contact plates are provided including a base member and a lid. The base member has an upwardly extending sidewall extending circumferentially around a peripheral edge portion thereof to define a sample receiving area. The lid has a sidewall extending circumferentially around a peripheral edge portion thereof. A plurality of ribs extend inwardly from an inner surface of the sidewall of the lid. The ribs are configured to provide an interference fit engagement between the sidewall of the base member and the sidewall of the lid when the lid is attached to the base member.

In further embodiments of the present invention, the base member includes a contact surface extending around the sidewall of the base member outside the sample receiving area. The lid includes a flange member extending outwardly from a bottom end of the sidewall of the lid and positioned to engage the contact surface of the base member when the lid is attached to the base member. The contact surface of the base member may also include a plurality of ribs extending upwardly therefrom and positioned to engage the flange member of the lid when the lid is attached to the base member. The ribs of the base member and the ribs of the lid may together define an airflow passage to the sample receiving area when the lid is attached to and secured to the base member.

In other embodiments of the present invention, the ribs of the lid are configured to provide a retention force of between about 50 grams and about 2000 grams when the lid is attached to the base member and the flange member engages the contact surface of the base member. The ribs of the lid may be configured to provide a retention force of at least about 50 grams when the lid is attached to the base member and the flange member of the lid engages the contact surface of the base member independent of the rotational orientation of the lid relative to the base member on repeated attaching of the lid to the base member.

In further embodiments of the present invention, the ribs of the lid taper inwardly at a first angle relative to a central axis of the contact plate. An outer surface of the sidewall of the base member tapers inwardly at a second angle relative to the central axis of the contact plate. The first angle and the second angle are selected to provide the interference fit engagement. The first angle may be between about 3.5 degrees and about 4.5 degrees and the second angle may be between about 3.5 degrees and about 4.5 degrees.

In other embodiments of the present invention, the ribs of the lid have a height relative to the inner surface of the sidewall of the lid at a bottom side of the lid of between about 0.02 centimeters (cm) and about 0.04 cm. The ribs extending from an inner surface of the lid may have a width of between about 0.04 centimeters (cm) and about 0.09 cm. The inner surface of the lid may have a minimum radius about equal to a maximum radius of the outer surface of the sidewall of the base member. The inner surface of the lid may have a minimum radius within about 0.03 cm of a maximum radius of the outer surface of the sidewall of the base member.

In further embodiments of the present invention, the plurality of ribs extending from an inner surface of the lid includes at least 4 ribs. In some embodiments, 4 ribs may be provided positioned about 90° apart around the inner surface of the lid. In other embodiments at least 12 ribs are provided. The at least 12 ribs may be positioned at substantially uniformly offset locations around the inner surface of the lid.

Objects of the present invention will be appreciated by those of ordinary skill in the art from a reading of the figures and the detailed description of the embodiments that follow, such description being merely illustrative of the present invention.

BRIEF DESCRIPTION OF THE DRAWINGS

The accompanying drawings, which form a part of the specification, illustrate embodiments of the present invention. The drawings and description together serve to fully explain the invention. In the drawings.

DETAILED DESCRIPTION OF THE PREFERRED EMBODIMENTS

Figure 1:
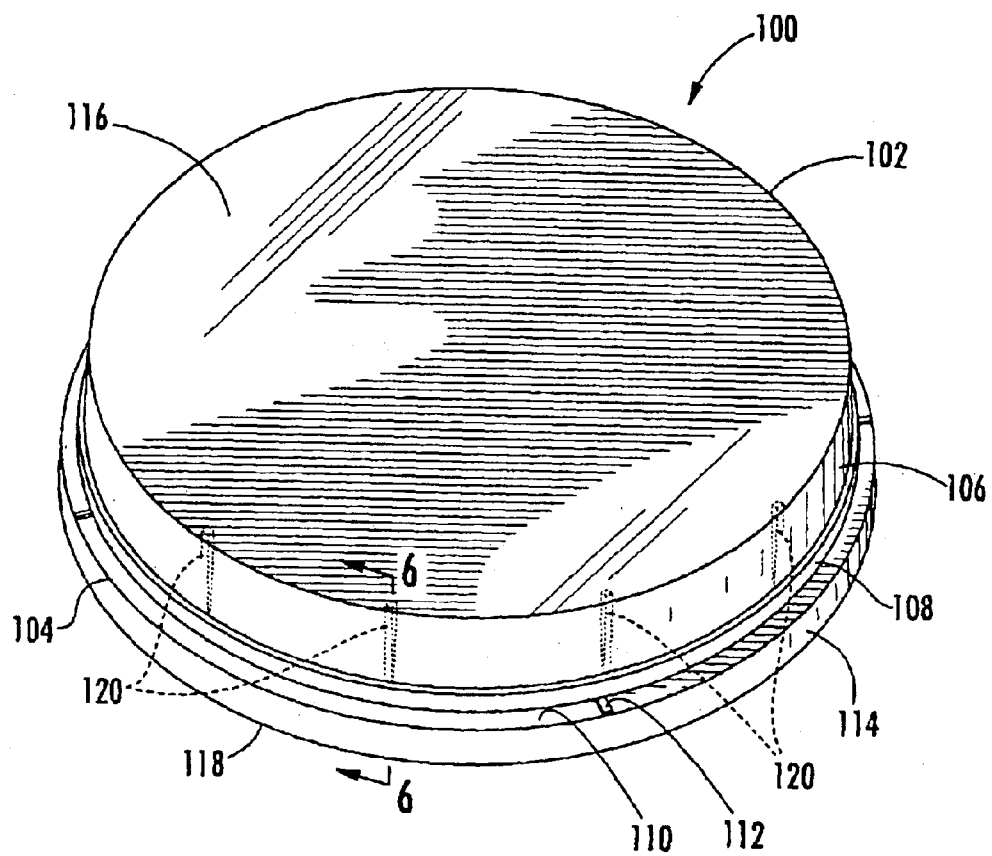
FIG. 1 is a perspective view of a contact plate in accordance with embodiments of the present invention.

The present invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. In the drawings, like numbers refer to like elements throughout. The terms "upwardly", "downwardly", "vertical", "horizontal", "bottom", "top" and the like are used herein for the purpose of explanation only and have there normal orientation with reference to use of the contact plates in sample testing.

Figure 2:
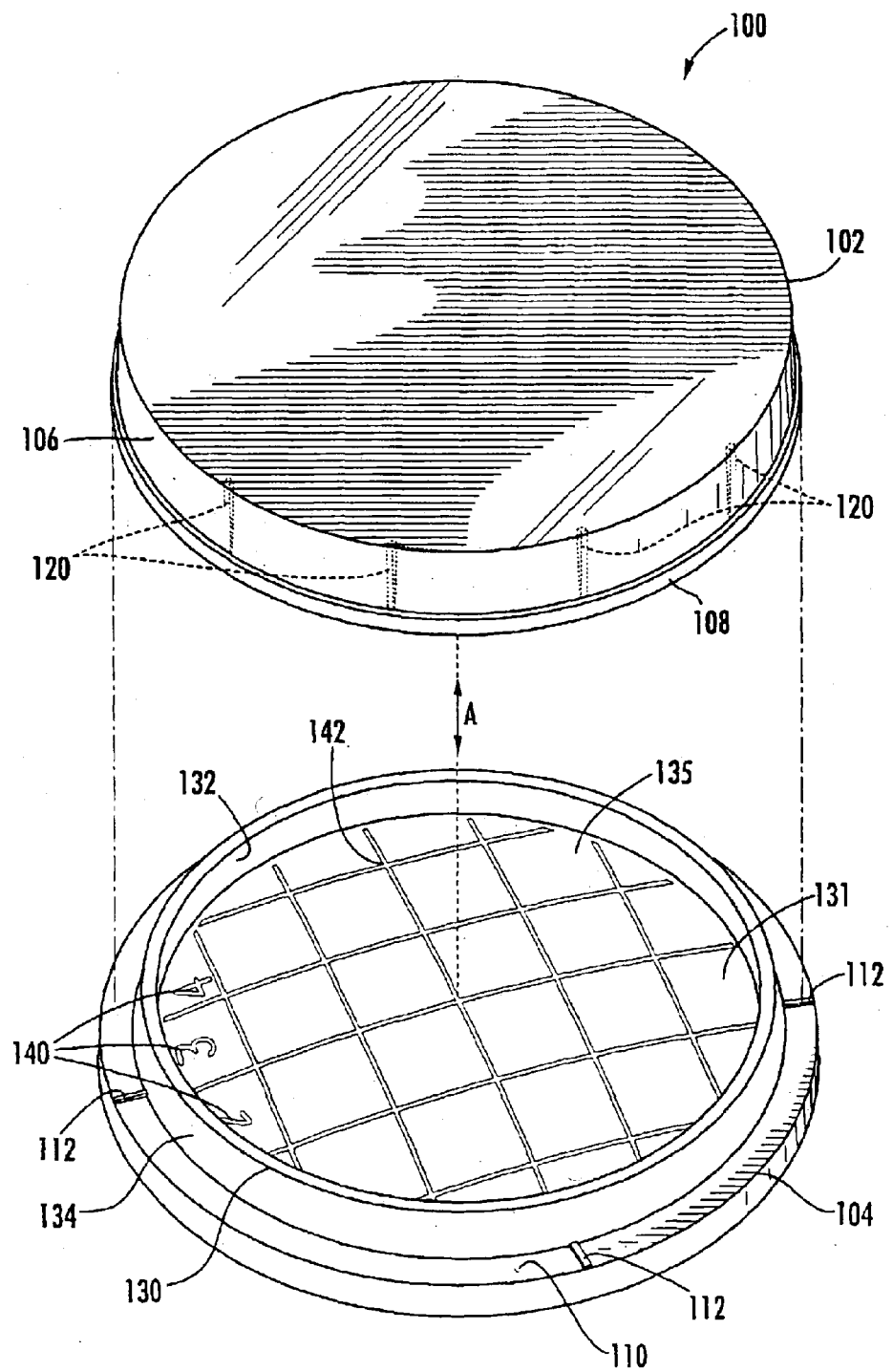
FIG. 2 is a perspective view of a lid and a base member of a contact plate in accordance with embodiments of the present invention in an open position.

Referring now to FIGS. 1–4, a contact plate in accordance with embodiments of the present invention will now be described. The contact plate 100 includes a lid 102 and a base member 104. The base member has a sidewall 130 (FIG. 2) extending circumferentially around a peripheral edge portion of the base member 104. As seen in FIG. 2, the side wall 130, in cooperation with the bottom wall (floor) 131, defines a sample receiving area 135 in which a sample growth media, such as agar, and/or samples to be evaluated may be contained. Preferably, a continuously extending side wall 130 is provided so that a growth media may be placed in the sample receiving area 135 in an agar form. The side wall 130 includes an outer surface 134 and an inner surface 132.

Figure 4:
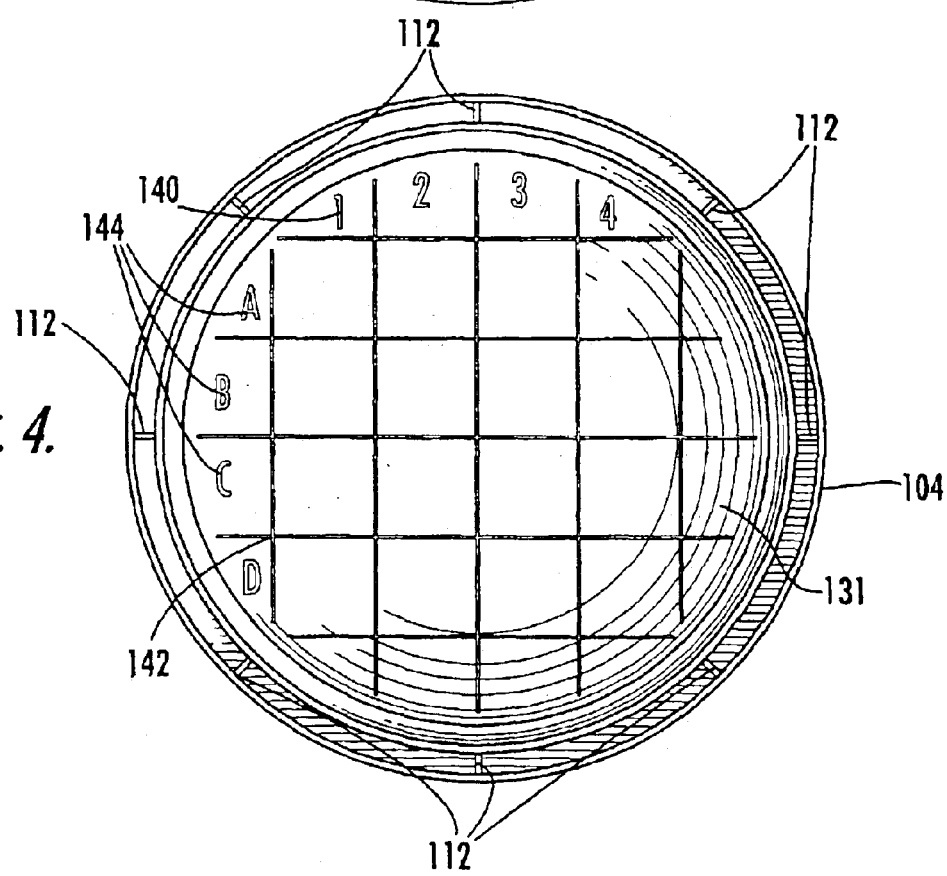
FIG. 4 is a planar top view of a base member of a contact plate in accordance with embodiments of the present invention.

The base member 104, as shown in FIG. 2, further includes a contact surface 110 extending around the side wall 130 outside the sample receiving area 135. A plurality of ribs 112 extend upwardly from the contact surface 110 and are positioned to engage a flange member 108 of the lid 102 when the lid 102 is attached to the base member 104 as illustrated in FIG. 1. Also shown in FIG. 2 or FIG. 4 are numerical indicia 140, grid indicia 142 and alpha numeric indicia 144, all of which may be used, for example, by reference to the grid indicia 142.

Lid 102 has a sidewall 106 extending circumferentially around a peripheral edge of the lid 102. A plurality of ribs 120 extend from an inner surface 122 (FIG. 3) of the side wall 106. The ribs 120 are configured to provide an interference fit engagement between the side wall 130 of the base member 104 and the side wall 106 of the lid 102 when the lid 102 is positioned and secured/attached to the base member 104.

Figure 5:
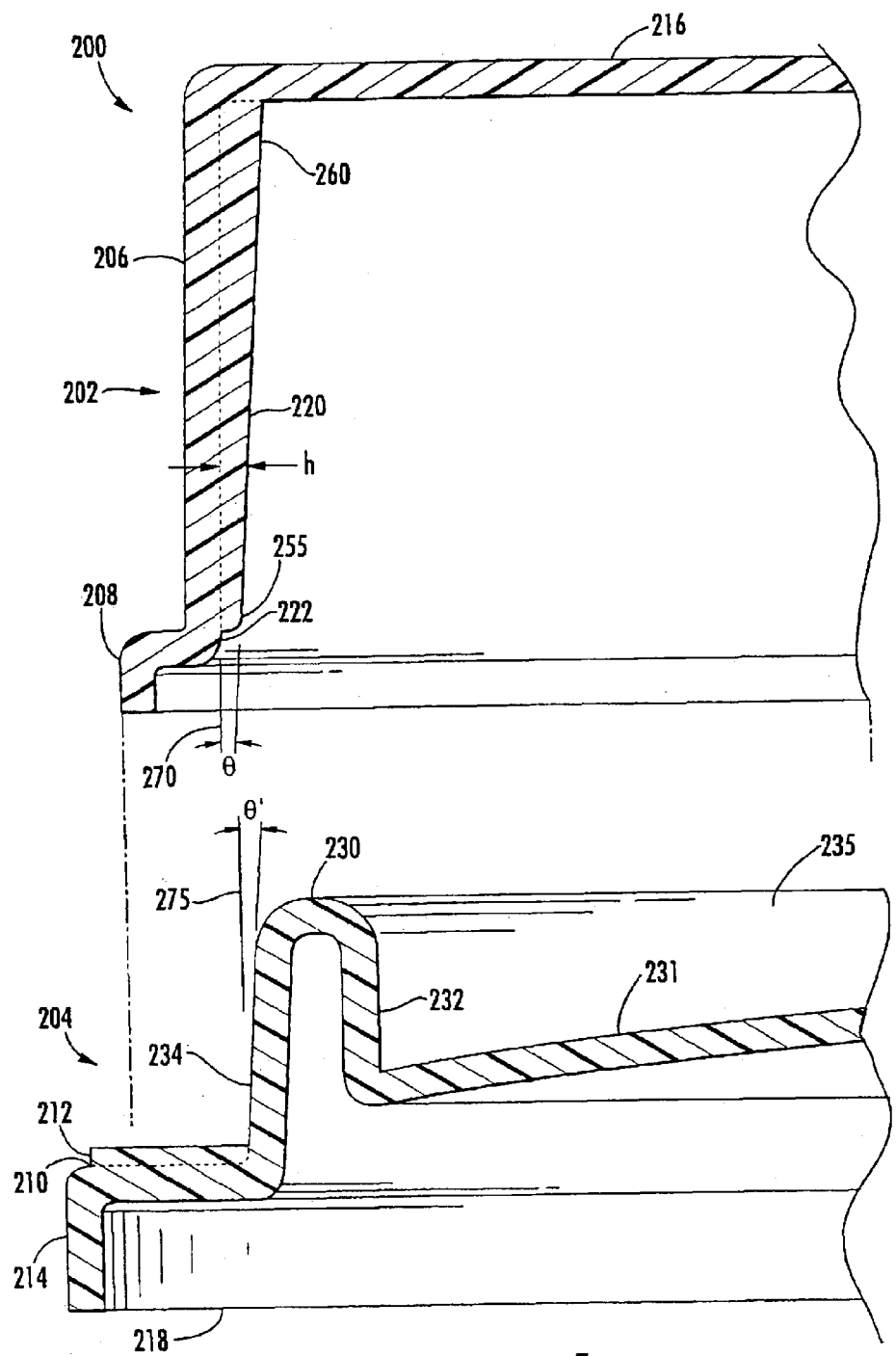
FIG. 5 is a partial cross-sectional view of a lid and a base member of a contact plate in accordance with embodiments of the present invention in an open position.
Figure 6:
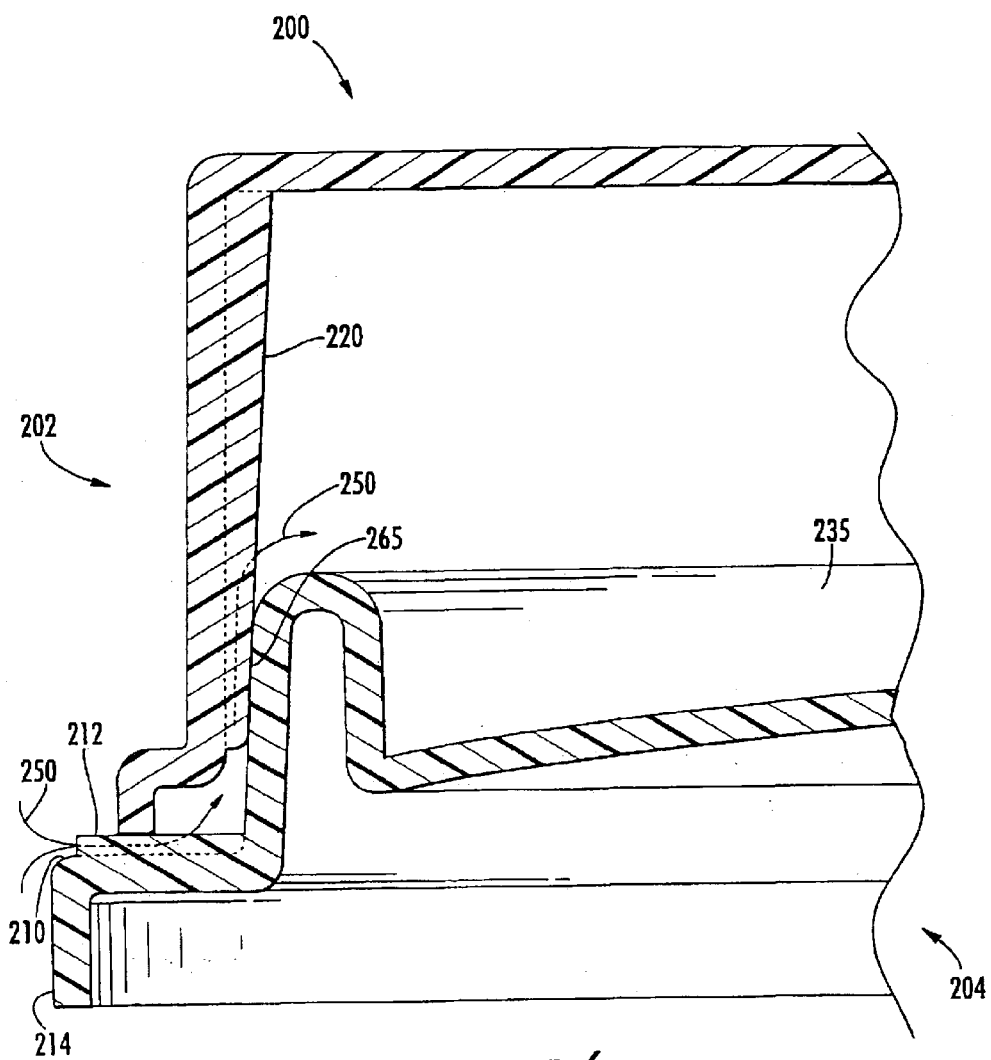
FIG. 6 is a partial cross-sectional view of the lid and a base member of FIG. 5 in a closed position.

Referring now to the partial cross sectional views of FIGS. 5 and 6, a contact plate 200 according to embodiments of the present invention will be further described. FIG. 5 shows a lid 202 and a base member 204 in an open/unattached/unsecured position, while FIG. 6 shows the lid 202 and base member 204 in a closed/secured/attached position with an interference fit engagement holding the lid 202 coupled to the base member 204. Like numbered features, of the 200 series, illustrated in FIGS. 5 and 6 correspond generally to the counterpart numbered features of the 100 series described with reference to FIGS. 1–4 above and will not be further described herein.

Figure 3:
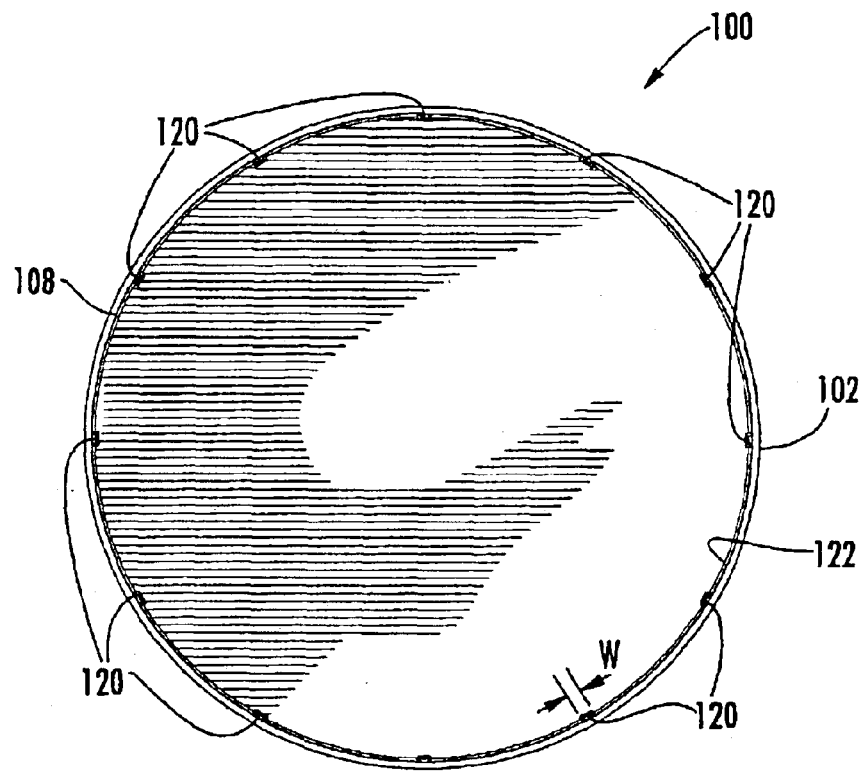
FIG. 3 is a planar top view of a lid of a contact plate in accordance with embodiments of the present invention.

As shown in FIGS. 5 and 6, by the cross-sectional view of the lid 202 through one of the ribs 220 and the cross-sectional view of the base member 204 through one of the ribs 212 on the contact surface 210 of the base member 204, the ribs 220 have a height h extending inwardly from an inner surface 222 of the side wall 206. The ribs 120, 220 similarly have a width w as illustrated in FIG. 3. As shown in FIG. 5, the ribs 120, 220 taper from a smaller height at a bottom end 255 of the lid 202 to a greater height at a top end 260 of the lid 202.

As shown in FIG. 6, the ribs 212 extending from the contact surface 210 of the base member 204 and the ribs 220 extending from the inner surface 222 of the lid 202 define an airflow passage 250 to the sample receiving area 235 when the lid 202 is attached to the base member 204. As also shown in FIG. 6, an interference fit engagement region 265 is provided between the ribs 220 and the outer surface 234 (FIG. 5) of the side walls 230 (FIG. 5). The side walls 230 further include an inner surface 232 defining the sample receiving area 235 with a single U-shaped wall member providing the side wall 230. The sample receiving area 235 is further defined by the bottom wall 231 on which indicia, such as the indicia 140, 142, 144, may be provided.

As shown in FIG. 5, the outer surface 234 of the base side wall 230 may be tapered at an angle $\theta'$, tapering in from a maximum radius 275 of the outer surface 234 of the side wall 230 relative to a central axis A (FIG. 2) of the contact plate 100, 200. In addition, the ribs 220 extending from the inner surface 222 of the lid 202 taper inwardly at an angle $\theta$ relative to the central axis A. The inner surface 222 of the lid 202 has an associated minimum radius 270. The angle $\theta$ and the angle $\theta'$ may be selected to provide the desired interference fit engagement between the lid 202 and the base member 204 when the lid 202 is positioned and secured in an attached position over the base member 204 with the flange member 208 extending from the side wall 206 of the lid 202 engaging the ribs 212 of the contact surface 210 of the base member 204. In various embodiments, the resulting frictional retention force is between about 50 grams and about 2000 grams.

It is to be understood that the retention force may be affected by the angles $\theta$, $\theta'$, the height h of the ribs 220 and the minimum radius 270 and maximum radius 275 of the lid 202 and the base member 204, respectively. It will be further understood that the frictional forces providing the interference fit engagement may be increased by increasing the width w of the ribs 120, 220 as well as by one or more of increasing the maximum radius 275 of the side walls 134, 234, by decreasing the minimum radius 270 of the side walls 106, 206, by increasing the height H of the ribs 120, 220 or by changing the relative angles $\theta$, $\theta'$.

In particular embodiments of the present invention, the ribs 120, 220 have a height h relative to the inner surface 122, 222 at the bottom side 255 of the lid 202 of between about 0.02 centimeters (cm) and about 0.04 cm. The ribs 120, 220 may have a width of between about 0.04 centimeters (cm) and about 0.09 centimeters (cm). The inner surface 122, 222 of the lid 102, 202 may have a minimum radius within about 0.03 cm of a maximum radius of the outer surface 134, 234 of the side wall 130, 230 of the base member 104, 204. The angle $\theta$ may be between about 3.5 degrees and about 4.5 degrees and the angle θ' may be between about 3.5 degrees and about 4.5 degrees.

In various embodiments of the present invention, different numbers of the ribs 120, 220 may be provided on the lid 102, 202. In various embodiments, there may be at least 4 ribs and at least 12 ribs, as illustrated by the 12 ribs shown for the embodiment illustrated in FIG. 3. The ribs may be positioned at substantially uniformly spaced locations around the inner surface 122, 222 of the side walls 106, 206 of the lid 102, 202. For example, in a 4 rib embodiment, the ribs 120, 220 may be positioned about 90 degrees apart around the inner surface 122, 222 of the lid 102, 202.

The lid 102, 202 and the base member 104, 204 may both be molded from the same material or from different materials. In particular embodiments of the present invention, the lid 102, 202 and the base member 104, 204 are comprised of a material selected from the group consisting of polycarbonate and polystyrene. Preferably, the lid member 102, 202 and the base member 104, 204 are molded from the same material.

Processes for molding lids 102, 202 and base members 104, 204 will be understood by those of skill in the art in light of the disclosure herein and will not be further described herein. However, it is to be understood that the side walls 106, 206 and the side walls 134, 234 as well as other illustrated features of the contact plates 100, 200 may be provided tapered angles selected to facilitate molding operations. In such configurations, it is to be understood that the reference angles relative to the axis A used for tapering of the features as described herein may affect the interference force provided and, thus, the specification of the height h with width w angles θ, θ' and maximum and minimum radiuses of the engaging features are to be considered with reference to such angled aspects of the various members, which may be included to facilitate molding operations.

The inclusion of the ribs 120, 220 extending inwardly from the side walls 106, 206 of the lid 102, 202 as described herein may provide potential benefits in facilitating molding and maintenance of molds used in manufacturing the contact plates 100, 200 of the present invention. For example, the selection of suitable inserts and other aspects of the mold for the inventive contact plates 100, 200 may allow the use of a four cavity, rather than two cavity, mold.

The inventors of the present invention have observed in the prior art contact plates that some deformation and creep may occur in the lid 102, 202 over time when subjected to pressure. As a result, in applications where the lid 102, 202 is removed and reinstalled over the base member 104, 204 repeatedly, the rotational orientation of the lid 102, 202 relative to the base member 104, 204 may change each time the lid 102, 202 is replaced on the base member 104, 204 and the deformation of the lid may cause the retention force therebetween to change each time. The inventors have found that the use of the ribs 120, 220 extending from the inner surface 122, 222 of the side walls 106,206 of the lid, as contrasted with ribs on the base member, may beneficially provide a retention force of a desired minimum amount, such as of at least about 50 grams, even on repeated pressing of the lid 102, 202 over the base member 104, 204 independent of the rotational orientation of the lid 102, 202 relative to the base member 104, 204.

Thus, a contact plate 100, 200 may be provided in accordance with embodiments of the present invention that provides a holding force to maintain a lid in a closed position relative to a base member and the holding force may be maintained at a desirable level to insure proper holding of the lid on the base member over repeated use, regardless of the rotational orientation used for the lid relative to the base member. Such benefits may be provided without otherwise changing the size and/or shape of the sample receiving area 135, 235 and the perception of the contact plate 100, 200 by a user. As a result, the number of accidental openings and operator-related contamination events may be reduced using an operator friendly one-touch closure with light pressure on the top center of the lid 102, 202.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed is:

1. A contact plate comprising:
   a base member having a sidewall extending circumferentially around a peripheral edge portion thereof define a sample receiving area; and
   a lid having a sidewall extending circumferentially around a peripheral edge portion thereof and a plurality of ribs extending from an inner surface thereof, the ribs being configured to provide an interference fit engagement between the sidewall of the base member and the sidewall of the lid when the lid is attached to the base member;
   wherein the ribs extending from an inner surface of the lid taper inwardly at a first angle relative to a central axis of the contact plate and an outer surface of the sidewall of the base member tapers inwardly at a second angle relative to the central axis of the contact plate.

2. The contact plate of claim 1 wherein the ribs extending from an inner surface of the lid have a height relative to the inner surface of the sidewall of the lid at a bottom end of the lid of between about 0.02 centimeters (cm) and about 0.04 cm.

3. The contact plate of claim 2 wherein the ribs extending from an inner surface of the lid have a width of between about 0.04 centimeters (cm) and about 0.09 cm.

4. The contact plate of claim 2 wherein the inner surface of the lid has a minimum radius about equal to a maximum radius of the outer surface of the sidewall of the base member.

5. The contact plate of claim 2 wherein the surface of the lid has a minimum radius within about 0.03 cm of a maximum radius of the outer surface of the sidewall of the base member.

6. The contact plate of claim 2 wherein the first angle is between about 3.5 degrees and about 4.5 degrees and the second angle is between about 3.5 degrees and about 4.5 degrees.

7. The contact plate of claim 2 wherein the plurality of ribs extending from an inner surface of the lid comprises at least 4 ribs.

8. The contact plate of claim 7 wherein the plurality of ribs extending from an inner surface of the lid comprises 4 ribs positioned about 90° apart around the inner surface of the lid.

9. The contact plate of claim 2 wherein the plurality of ribs extending from an inner surface of the lid comprises at least 12 ribs.

10. The contact plate of claim 9 wherein the at least 12 ribs are positioned at substantially uniformly offset locations around the inner surface of the lid.

11. The contact plate of claim 1 wherein the first angle is between about 3.5 degrees and about 4.5 degrees and the second angle is between about 3.5 degrees and about 4.5 degrees.

* * * * *